United States Patent [19]

Wentzell et al.

[11] Patent Number: 4,526,037
[45] Date of Patent: Jul. 2, 1985

[54] NOZZLE INNER RADIUS INSPECTION SYSTEM

[75] Inventors: Timothy H. Wentzell, South Windsor, Conn.; Zoran Kuljis, Zagreb, Yugoslavia

[73] Assignee: Combustion Engineering, Inc., Windsor, Conn.

[21] Appl. No.: 503,978

[22] Filed: Jun. 13, 1983

[51] Int. Cl.³ .................. G01N 29/04; G21C 17/00
[52] U.S. Cl. ........................... 73/640; 73/634; 73/635; 73/637; 376/249; 376/252
[58] Field of Search ............. 73/634, 635, 637, 640; 376/249, 252

[56] References Cited

U.S. PATENT DOCUMENTS

| | | | |
|---|---|---|---|
| 3,593,120 | 7/1971 | Mandula, Jr. | 73/635 |
| 3,863,496 | 2/1975 | Hiramatsu et al. | 73/634 |
| 3,929,007 | 12/1975 | Dent et al. | 73/637 |
| 4,117,733 | 10/1978 | Gugel | 73/634 |
| 4,169,758 | 10/1979 | Blackstone et al. | 376/249 |
| 4,368,644 | 1/1983 | Wentzell et al. | 73/634 |

Primary Examiner—Howard A. Birmiel
Attorney, Agent, or Firm—Arthur L. Wade

[57] ABSTRACT

The lip of the inner radius of a nozzle mounted through the wall of a nuclear reactor vessel is sandwiched between a transmitter and receiver of ultrasonic sound. The transmitter scans the internal surface of the nozzle lip while maintained a constant average distance from a receiver scanning the nozzle surface on the reactor vessel side of the lip. The two surfaces intersecting to form the inner radius vary in angle as the surfaces are scanned by the transmitter and receiver. Linkage is shown between the transmitter/receiver and the boom with which they are caused to sweep the lip to simultaneously accommodate the saddle shape of the inner radius and the varying angle between the lip surfaces.

6 Claims, 4 Drawing Figures

NOZZLE INNER RADIUS INSPECTION SYSTEM

TECHNICAL FIELD

The present invention relates to the coordination of a nondestructive ultrasonic sound transmitter and receiver over the surfaces of the inner radius lip of a nuclear vessel nozzle. More particularly, the invention relates to ultrasonic inspection scanning of the lip which is the material on each side of the inner radius of nozzles mounted through the walls of nuclear reactor vessels to detect postulated fractures beneath the cladding.

BACKGROUND ART

The disclosure of this invention is to be contrasted with and compared to the disclosure of the invention in U.S. Pat. No. 4,368,644, Wentzell, et al. issued Jan. 18, 1983. Further, as may appear appropriate, the disclosure of this patent is to be considered as incorporated in and made a part of this present disclosure. Clearly, both inventions relate to apparatus with which to carry out the nondestructive ultrasonic inspection of nuclear reactor systems in adjacent locations.

For a utility operating a nuclear reactor system, it is imperative that Inservice Inspection (ISI) of the reactor system vessels be performed as rapidly as possible without sacrificing accuracy. The inspection system is comprised of mechanical positioning equipment and nondestructive examination instrumentation. It is desirable to reduce the time in making these inspections without reducing the quality of the examinations. Reduction in this time will enable the utility to realize savings in operating costs due to shorter downtimes and a reduction in radiation exposure to examination personnel.

The present rules for ISI, established by the ASME Code, Section XI "Rule for Inservice Inspection of Nuclear Power Plant Components", require a complete inspection of reactor vessel components every ten operational years. In addition it is a USNRC requirement that personnel radiation exposure be "as low as reasonably achievable." Hence, it is inevitable, based on these criteria and the very high cost of plant downtime, that an inspection must be carried out with reliable, accurate, and rapid techniques.

The inservice inspection program includes both the component and piping bodies. In general, there are numerous access problems, body configuration variations, and radiation hazards that must be considered. The inservice inspection tool may be mounted from the flange of the nuclear vessel and manipulated beneath many feet of radiation-shielding water. The area to be inspected in and about the nuclear vessel is reached with predetermined location information, supplemented by TV cameras. The ISI tool, from its mount on the reactor vessel flange, is capable of reaching all areas of the reactor vessel by actuating rotating and telescoping booms along with specially designed fixtures that hold nondestructive ultrasonic search units.

The operating console for this tool contains the necessary controls and instruments for manifesting readout information from the detectors. The controller allows the operator to move the search units accurately through all the required regions to be examined and provides precise position data. By enhancing the versatility of the inspection equipment, the number and frequency of mechanical configuration changes can be reduced. This has resulted in a reduction in setup time and, equally important, greatly reduced handling of contaminated parts. This versatility is achieved by means of remote or preprogrammed positioning of ultrasonic transmitters and receivers.

There is a need for supporting linkage between an ultrasonic sound transmitter and receiver as the transmitter and receiver are swept about the surfaces of an inner radius lip of a nozzle in a nuclear reactor vessel. The linkage must accommodate the varying angle between the nozzle side and vessel side of the inner radius lip while simultaneously accommodating the saddle shape of the inner radius as the boom is rotated in a 360° sweep.

DISCLOSURE OF THE INVENTION

The present invention contemplates a connection between a transmitter of ultrasonic sound and a receiver to move them over their respective surfaces of a nozzle inner radius lip while maintaining a constant average distance between the transmitter and receiver.

The invention further contemplates sweeping the surfaces of the lip of the inner radius of a nuclear reactor vessel nozzle by linkage between the transmitter and receiver which maintains the transmitter and receiver an average distance between them as the surfaces vary in angle to each other from the inner radius.

The invention further contemplates a transmitter and receiver of ultrasonic sound linked to maintain the transmitter and receiver at a constant average distance between them as the linkage is carried in a sweep of the inner radius on a boom whose axis coincides with the centerline of the nozzle.

The invention further contemplates a pair of receivers oriented relative to a single transmitter during the sweep of the inner radius lip so that a first of the receivers receives its maximum reflected sound from the transmitter at the 9 and 3 o'clock positions of the sweep, while the second of the receivers receives its maximum sound from the transmitter at the 6 and 12 o'clock positions of the sweep, the response of both receivers being combined to detect anomalies in the material of the inner radius lip of the nozzle.

Other objects, advantages and features of this invention will be become apparent to one skilled in the art upon consideration of the written specification, appended claims, and attached drawings.

BRIEF DESIGNATION OF THE DRAWINGS

Figure 2:
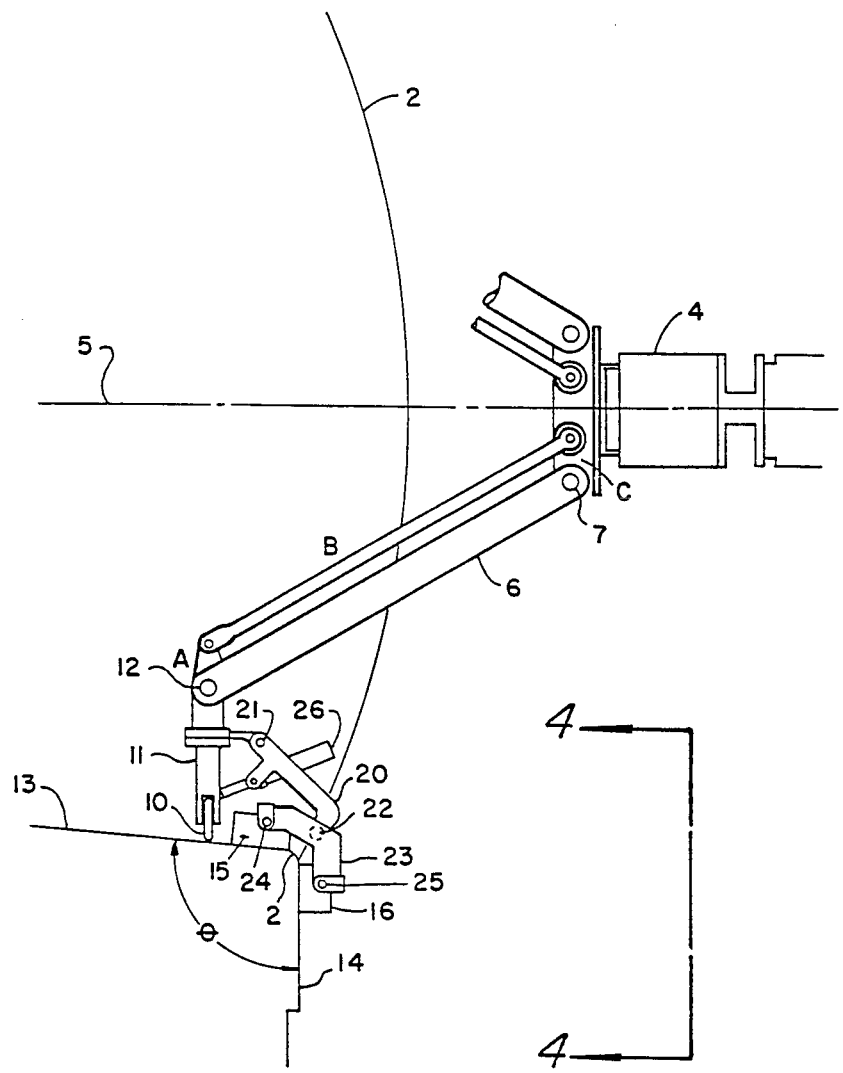
FIG. 2 is a sectioned side elevation of the nozzle lip and inspecting apparatus of FIG. 1.
Figure 3:
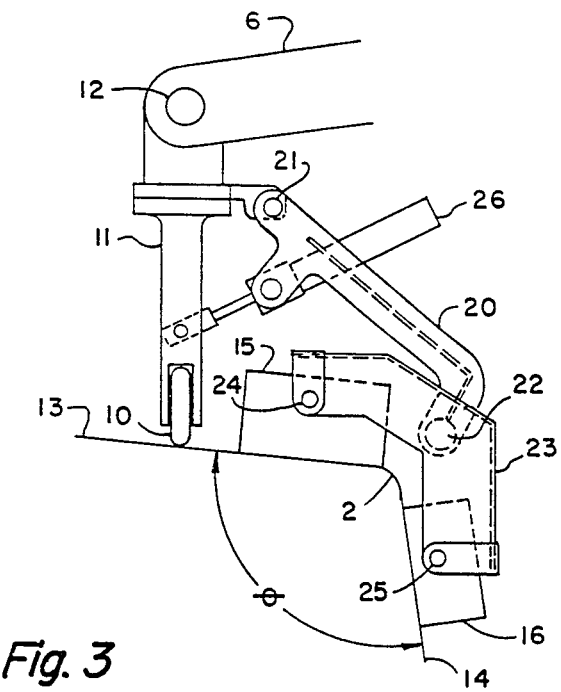
Figure 4:
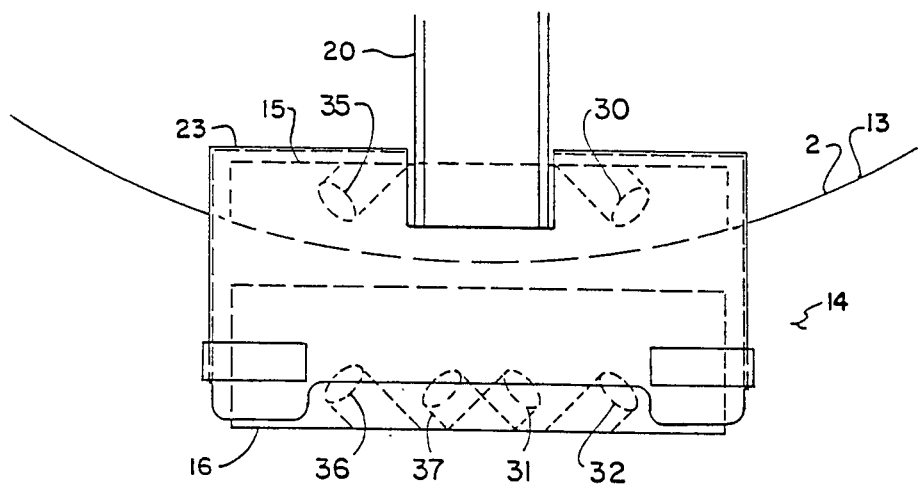

FIG. 3 is the inspection transmitter and receiver sleds of FIG. 2 positioned on the inner radius lip surfaces at the 9 and 3 o'clock positions of the sweep; and FIG. 4 is an elevation in the direction of lines 4—4 of FIG. 2.

BEST MODE FOR CARRYING OUT THE INVENTION

General Organization

In reorientation of the problem, the present invention faces the task of bringing nondestructive ultrasonic sound to bear on the lip of the inner radius of a reactor vessel nozzle. Specifically, ultrasonic sound can be projected into metallic bodies for detection by a receiver. Any anomaly, defect, flaw, etc. will reflect the ultrasonic sound for a seemingly magic interpretation by an electronic network. The present disclosure will not extend to an analysis of the electronic network which manifests the received energy, rather the disclosure will focus upon the structure required to mechanically position the transmitter and receiver on each side of the material of the nozzle lip at the inner radius. It is the geometric shape of this lip which presents the problem.

The inner radius of the nozzle is the edge at which the inner surface of the nozzle meets the inner surface of the vessel. Unfortunately, for movements of the transmitter and receiver over their surfaces for inspection purposes, the radius is not a simple circle. The nozzle is a conduit of circular cross section, but the cross section radius is significantly smaller than the radius of the vessel wall it penetrates. Thus, the inner radius is geometrically the intersection of two cylinders having significantly different diameters. With the end of the nozzle shaped to conform to the radius of the inner surface of the vessel, the inner radius of the nozzle can best be described as "saddle shaped". Further, as the inner radius is swept by the inspection apparatus, the angle Theta, formed by the two surfaces of the lip, varies. This angle Theta is at its largest value at the 3 and 9 o'clock positions of the sweep and, of course, at its smallest value at the 6 and 12 o'clock positions.

Disclosure of the structure will begin with a boom rotated about a center which coincides with the centerline of the nozzle. Pivoted from the boom is an arm whose second end is extended down toward the lip to be swept and inspected. The second end of the arm is basically supported by a roller which follows the internal cylindrical surface of the nozzle. Mounted on this base structure is the linkage supporting the sleds for transmitters and receivers of ultrasonic sound. These sleds are carried by the linkage structure depending from the second end of the arm to follow the surfaces of the lip as the surfaces vary in their angle Theta, and as the arm is swept by the boom which is rotated and translated about and along the centerline of the nozzle, as dictated by the saddle shape of the inner radius.

The number and locations of the transmitters and receivers on their sleds are significant; however the drawing figures will first solidify understanding of the relationship between the boom, the arm, and the linkage between the arm and the sleds relative to the two sides of the lip which intersect to define the inner radius. The resolution of the signals received from the transmitters is a matter of electronic manipulation and is a further matter not of present concern, important as it may be to complete the inspection. The present invention is concerned with mechanically positioning the transmitter and receiver sleds relative the sides of the lip of the nozzle inner radius.

A View From Within The Vessel

Figure 1:
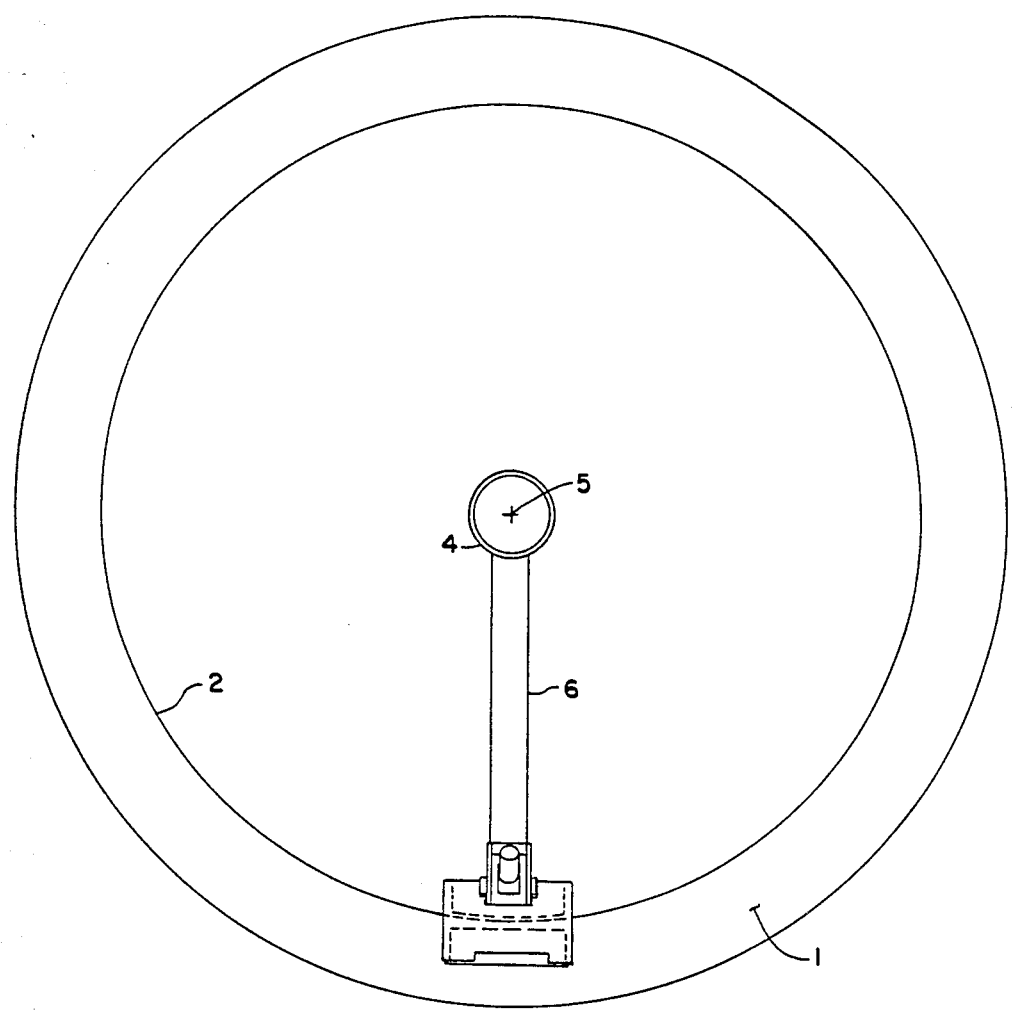
FIG. 1 is an elevation of the vessel end of a nuclear reactor nozzle whose inner radius lip is inspected by apparatus embodying the present invention.

FIG. 1 is selected as a first means of overall orientation of the relationship between nozzle 1 and the inspection structure. The nozzle, seen from within the vessel in elevation, has its inner radius 2 appear as a circle. The vessel wall 3 is penetrated by nozzle 1. Of course, the nozzle is welded to the vessel wall 3. The inspection structure embodying the present invention begins with boom 4 which is lowered into position at the centerline 5 of nozzle 1. How boom 4 is supported and rotated and translated along centerline 5 will not be included in the disclosure. The boom is simply evidenced in the form of a cylindrical hub and the structure embodying the invention is pivoted from this boom/hub 4. Evidence of the novel inspection structure is indicated by an arm 6. Boom hub 4 rotates about centerline 5 and in doing so, sweeps the second end of arm 6 sequentially from the 6 o'clock position shown, through the 9, 12 and 3 o'clock positions, returning to the 6 o'clock position. Of course, the sweep could be made in the reverse direction, the clockwise direction sweep being spoken of only as a matter of instinctive first choice.

Sectioning The Nozzle In Side Elevation

FIG. 2 gives us a comprehensive disclosure of the relationship between boom 4, arm 6, and the transmitter/receiver sleds sandwiching the lip of inner radius 2. Arm 6 and the sleds attached to it are shown while inspecting the lip surfaces. The position the structure has prior to taking the FIG. 2 position is not disclosed. FIG. 2 shows the sleds as having arrived at their inspection positions and the explanation of the linkage between the sleds and arm 6 as the inner radius of the lip is swept can be understood.

First, arm 6 is pivoted by its first end from boom 4 at pivot 7. The structure by which arm 6 is brought to this position is not disclosed. The second end of arm 6 carries roller 10 by means of post 11. Post 11 is pivoted at its upper end from the second end of arm 6 at pivot point 12. The structure which controls the angle of post 11 with arm 6 is not disclosed in detail. It is simple enough to understand that arm 6 is brought to the position shown in FIG. 2 and forms a stable base with the contact of roller 10 with lip surface 13 and maintains parallelism by means of the parallelogram formed by link A, B, C, and 6. Thus, it can be appreciated that as boom 4 translates along and rotates about centerline 5, roller 10 maintains contact with the internal cyclindrical surface of the nozzle as an extension of the lip surface 13. Of course, the surface of nozzle 1 is concentric to its centerline 5 and, therefore, no change is made in the angle arm 6 makes with centerline 5 during inspection movements. As boom 6 is retracting from the inspection position of FIG. 2 for removal, arm 6 may be pivoted upward, and mechanism may be provided to control the angle post 11 makes with arm 6 for purposes of clearing the mechanism from the bore of nozzle 1. All of this arrangement is adjunct, preliminary to the arrival and removal of roller 10 with contact on surface 13.

To proceed with the disclosure, it must be appreciated that FIG. 2 illustrates arm 6, post 11, and roller 10 as a fixed base for the support of transmitter and receiver sleds. Next, in order of importance, is the disclosure of nozzle surface 14 which intersects surface 13 to form inner radius 2. The angles formed by these two surfaces is designated as Theta. The value of Theta varies as a sweep is made of inner radius 2. It is the variation of angle Theta that the support structure for sleds 15 and 16 must accommodate, the sleds being ultrasonic transducer holders. This accommodation must maintain an average distance between the transmitter of ultrasonic sound mounted on sled 15 and the receivers mounted on sled 16 as the sleds scan the inner radius lip formed by surfaces 13 and 14.

The saddle shape of inner radius 2 was not obvious in FIG. 1. Enough of the outline of this saddle shape appears in FIG. 2 to disclose the necessity for partial accommodation of the variation in the sweep of the saddle shape by translation of boom 4 over a range along centerline 5 to maintain the sleds in uniform contact with surfaces 13 and 14. Again, the mechanism which powers boom 4 along centerline 5 in translation is not a part of the present disclosure. It is enough to analyze the movement of the linkage between the second end of arm 6 and the sleds 15 and 16 as the translation is made during the simultaneous sweep of inner radius 2.

Next, base link 20 is pivoted from its first end at 21. Pivot 21 is carried on post 11 and is, therefore, given a stable consistent relationship to centerline 5 as the sweep and translation of inspection is carried out. The second end of base link 20 carries a pivot 22. From pivot 22 a so-called seesaw link 23 is carried. Seesaw link 23 has each end more or less directly connected to a sled. In more detail, as far as seesaw link 23 is concerned, pivot 22 is roughly at its midpoint between its ends while the first end is connected to sled 15 and the second end is connected to sled 16. The sleds are not connected rigidly to the ends of seesaw link 23. A pivot 24 is formed between sled 15 and the first end of seesaw link 23, while pivot 25 is provided between the second end of link 23 and sled 16. All pivots (21, 22, 24 and 25) allow their linkages movement along arcs parallel to or in the plane of arm 6 and post 11. As base link 20 is pivoted about its first end pivot 21 clockwise, the sleds attached to the ends are brought against surfaces 13 and 14. As the angle Theta varies, seesaw link 23 pivots at 22 and sleds 15 and 16 pivot at 24 and 25 to maintain a uniform relationship between each sled and its respective lip surface.

A resilient force is applied to base link 20 in a clockwise direction to maintain the sled-to-surface contact during the inspection movement. A piston cylinder connection between post 11 and base link 20 is disclosed at 26. Although it is feasible to energize this piston cylinder 26 by pneumatic pressure to generate resilient force in the direction required to rotate base link 20, a spring structure may be utilized with proper design. Finally, rotating the base link structure about pivot point 21 combines with the translation of boom 4 to accommodate the saddle shape of the inner radius.

Variations In Angle Theta

FIG. 3 is offered as disclosure of the large value of angle Theta at the 9 and 3 o'clock positions of the sweep. The large angle Theta of FIG. 3 is to be compared with the relatively small angle Theta of FIG. 2. As disclosed, base link 20 pivots about point 21, seesaw link 23 pivots about point 22, sled 15 pivots about point 24, and sled 16 pivots about point 25 as required to accommodate the change in angle Theta during the 360° sweep of inspection. By "accommodation", of course, is meant the adjustment of this pivoted linkage between the sleds and the second end of arm 6 to maintain the sleds a constant average distance apart and uniformly related to the surfaces they respectively scan. With FIG. 2 disclosing the sleds at the 6 or 12 o'clock positions of the sweep, and FIG. 3 showing the same sleds at the 9 and 3 o'clock positions, the range of angle Theta is disclosed. This disclosure leads to that of FIG. 4 wherein an analysis is made of the orientation of the transmitters and receivers mounted on sleds 15 and 16.

Transmitters And Receivers On Their Sleds

Again, sleds 15 and 16 are disclosed at their 6 o'clock positions of FIGS. 1 and 2. Only the sleds are shown in relation to the inner radius lip 2 and its surfaces 13 and 14. In order to maximize the ultrasonic sound received from the transmitters, two transmitters are mounted on sled 15 and a pair of receivers for each transmitter are mounted on sled 16. Specifically, transmitter 30 is disclosed as mounted on sled 15, and receivers 31 and 32 are indicated as mounted on sled 16. Transmitters 30 is oriented to direct its sound into lip 2 obliquely with respect to the plane in which the linkage between the sleds move at the end of arm 6. This plane, of course, includes the centerline 5 during the sweep. Receivers 31 and 32 are directed to receive any sound as may be reflected by a defect. Further, one of the receivers, say receiver 32, is oriented to receive the maximum signal from transmitter 30 at the 6 and 12 o'clock positions, while receiver 31 is oriented to receive its maximum signal from the transmitter at the 9 and 3 o'clock positions. Any signals generated by receivers 31 and 32 are combined by remote stations to give a composite manifestation. As the sweep progresses sequentially through the various positions, the combined signals from the receiver manifest the location of any anomaly, flaw, or defect in lip 2.

To extend the area inspected, a second transmitter 35 is mounted on sled 15 and receivers 36 and 37 are mounted on sled 16. Transmitter 35 and receivers 36 and 37 are oriented on their respective sleds to project a field of inspection obliquely with respect to the plane as a mirror image of the field of transmitter 30 and receivers 31 and 32.

Again, perhaps unnecessarily, it is emphasized that the inspection is for anomalies in the lip material beneath its cladding. The disclosure has not dwelt extensively on the existence of the cladding of the internal nozzle surface. Nevertheless, one of the reasons for the adoption of this nondestructive form of inspection is to ferret out these defects which lurk below the surface of the cladding of lip 2.

Conclusion

The novelty embodied in the linkage between the boom hub 4 and the sleds 15 and 16 has been disclosed. With this linkage and the translation of the boom hub along the centerline of the nozzle, both the saddle shape of the inner radius of lip 2 and the variations in angle Theta are accommodated during the inspection sweep to maintain sleds 15 and 16 in proper relationship to each other. Secondly, the orientation of the transmitters on sled 15, and the receivers on sled 16 is maintained to provide a composite signal from the receivers which will be a maximum at all positions of the sweep.

One detail of the arrangement has not been emphasized sufficiently. Elongated arm 6 may not be the only arm pivoted from boom hub 4. At this late date, a fragment of arm 6a is indicated as pivoted from boom hub 4. With arm 6a, transmitter and receiver sleds are extended to the nozzle surface 180° from that portion of the surface inspected by sleds 15 and 16. The type of inspection made by the structure attached to arm 6a is of present concern only to point out that such second inspection can be made sequentially with the inspection of arm 6. Base link 20 can be pivoted upward from its position in FIG. 2 by actuator 26 as boom hub 4 is translated into the interior of the nozzle for the second inspection of arm 6a. However, the dominant features of the present invention remain embodied in the flexibility of the linkage arrangement which can be said to extend from boom hub 4 to sleds 15 and 16.

The first feature of the linkage of arm 6 begins with bringing roller 10 down upon surface 13 to form the fixed base. Pivot point 21 is thereby stabilized, established uniformly from centerline 5 as the sweep is made. The elongated base link 20 is then formed between the second end of arm 6 and seesaw link 23. Seesaw link 23 has its one end attached to pivot sled 15, while the other end of seesaw link 23 is attached to pivot sled 16. As the angle between the lip surfaces varies, all the pivots adjust relative to pivot 21 to maintain the sleds uniformly in contact with their scanned lip surfaces, while they are maintained a constant average distance from each other. One final point of accommodation is to contemplate the division of adjustment made between translation of boom hub 4 and the accommodation of the pivots. In the actual reduction to practice, the major portion of rough cut of the accommodation is made between translation, and the vernier adjustment is made by pivoting.

In extension of the above concept under which the sleds are positioned during the sweep, the transmitter or transmitters on sled 15 direct ultrasonic sound obliquely into the body of the inner radius lip while the receivers of sled 16 are oriented to catch any sound reflected from anomalies which have developed in the body of the lip.

From the foregoing, it will be seen that this invention is one well adapted to attain all of the ends and objects hereinabove set forth, together with other advantages which are obvious and inherent to the apparatus.

It will be understood that certain features and subcombinations are of utility and may be employed without reference to other features and subcombinations. This is contemplated by and is within the scope of the invention.

As many possible embodiments may be made of the invention without departing from the scope thereof, it is to be understood that all matter herein set forth or shown in the accompanying drawings is to be interpreted in an illustrative and not in a limiting sense.

We claim:

1. A nondestructive inspection apparatus for the inner radius lip of a nuclear reactor vessel nozzle which apparatus includes a boom hub whose axis coincides with the centerline of the nozzle and is adapted to rotate about and horizontally translate along the nozzle axis, including,
    a first elongated arm pivoted by its first end from the forward end of the boom hub,
    a roller connected to the second end of the elongated arm which is pivoted from the hub to engage the roller with the cylindrical internal surface of the nozzle as the boom hub is rotated in a sweep about the centerline and translated along the centerline,
    an elongated base link pivoted by its first end relative to the second end of the arm,
    a transmitter of ultrasonic sound connected to the second end of the base link adapted to move over and direct ultrasonic sound through the inner radius nozzle lip toward the interior of the reactor vessel,
    a receiver of the sound from the transmitter connected to the base link and positioned to move over the nozzle surface which forms the inner radius with the internal nozzle surface,
    and a means connected between the base link and the elongated arm arranged to generate a force on the base link to rotate the second end of the base link and the attached transmitter and receiver toward the lip surfaces,
    whereby pivoting of the base link and translation of the boom hub combine to accommodate the saddle shape configuration of the inner radius in maintaining the transmitter and receiver a constant average distance from each other as the boom hub rotates the arm in sweeping the circumference of the nozzle lip.

2. The inspection apparatus of claim 1, wherein,
    the base link is connected by its second end to the transmitter and receiver through a seesaw linkage pivoted between its ends,
    and the transmitter and receiver are each connected to an end of the seesaw link by pivots which provide for accommodation to the angle formed between the surfaces defining the inner radius.

3. The inspection apparatus of claim 2, wherein,
    dual receivers are pivoted from one end of the seesaw link and oriented so that one of the receivers is aligned to receive the strongest signal from the transmitter at the 6 and 12 o'clock positions of the sweep while the other receiver is aligned to receive the strongest signal from the transmitter at the 9 and 3 o'clock positions of the sweep,
    whereby the two receptions of the dual receivers are combined into a single signal over the complete sweep.

4. An inspection apparatus for the lip of the inner radius of a nozzle penetrating the wall of a nuclear reactor vessel, including,
    a transmitter sled positioned on the internal surface of the nozzle as one lip surface and in a plane including the nozzle centerline,
    a receiver sled positioned on the other lip surface and in the plane including the centerline,
    a seesaw link connected to each sled through pivots which maintain the sleds a constant average distance from each other as the sleds are moved along the lip surfaces on each side of the inner radius,
    an elongated arm pivoted by its first end from a boom hub carried at the centerline of the nozzle and mounting a roller at its second end engaging the inner surface of the nozzle,
    a base link pivoted from its first end to the second end of the elongated arm and connected to the middle of the seesaw link through a pivot at its second end,
    and means generating a resilient force connected to the base link to pivot the base link about its first end and thereby urge the sleds toward their lip surfaces,
    whereby the boom hub is rotated and translated at and around the centerline of the nozzle while the base link is resiliently urged to pivot from its first end to maintain the sleds of their lip surfaces as the angle varies during the sweep of the inner radius.

5. The inspection apparatus of claim 4, wherein,
    the means for resiliently pivoting the base link from its first end is a spring connecting at a point intermediate its ends and a point on the elongated first arm.

6. The inspection apparatus of claim 4, including,
    a transmitter of ultrasonic sound mounted on the transmitter sled and oriented to direct its sound at an angle to the plane including the nozzle centerline and the sleds,
    a first receiver mounted on the receiver sled and oriented to receive transmitted sound reflected from a defect in the lip at maximum strength when the sweep is at its 6 and 12 o'clock positions,
    a second receiver mounted on the receiver sled and oriented to receive transmitted sound reflected from a defect in the lip at maximum strength when the sweep is at its 9 and 3 o'clock positions,
    and manifesting means connected to both receivers to combine the signals of reflected sound continuously during the sweep.

* * * * *